US00PP10540P

United States Patent [19]

Poulsen

[11] Patent Number: Plant 10,540

[45] Date of Patent: Aug. 4, 1998

[54] ELATIOR BEGONIA PLANT NAMED 'DINA'

[75] Inventor: Jens Nørgaard Poulsen, Lisbjerg, Denmark

[73] Assignee: D.S. Cole Growers, Inc., Loudon, N.H.

[21] Appl. No.: 853,814

[22] Filed: May 9, 1997

[51] Int. Cl.[6] ..... A01H 5/00

[52] U.S. Cl. ..... Plt./87.18

[58] Field of Search ..... Plt./87.18

*Primary Examiner*—James R. Feyrer

*Attorney, Agent, or Firm*—C. A. Whealy

[57] ABSTRACT

A distinctive cultivar of Elatior Begonia plant named Dina, characterized by its numerous fully pink flowers with darker pink petal margin; upright, spreading and moderately vigorous growth habit; freely branching; good stem and stem base strength; dark green foliage; strong and vigorous root system that develops rapidly; resistant to Powdery Mildew under greenhouse conditions; and excellent postproduction longevity.

1 Drawing Sheet

The present invention relates to a new and distinctive cultivar of Begonia plant, botanically known as *Begonia× hiemalis*, commercially known as Elatior Begonia, and hereinafter referred to by the cultivar name Dina.

The new cultivar was discovered by the inventor in Aarhus, Denmark, as a mutation of the Elatior Begonia cultivar Lea (disclosed in U.S. Plant Pat. No. 9,561), and was observed in a group of 15-cm flowering plants of the parent cultivar in Feb., 1994.

Asexual reproduction of the new cultivar by terminal cuttings in Aarhus, Denmark, has shown that the unique features of this new Elatior Begonia are stable and are reproduced true to type in successive propagations.

The new cultivar has not been observed under all possible environmental conditions. The phenotype may vary significantly with variations in environment such as temperature, light level and daylength, without, however, any variance in genotype.

The following traits have been repeatedly observed and are determined to be the unique characteristics of Dina:

1. Numerous fully double pink flowers with darker pink petal margin.
2. Upright, spreading and moderately vigorous growth habit.
3. Freely branching.
4. Good stem and stem base strength.
5. Dark green foliage.
6. Strong and vigorous root system that develops rapidly.
7. Resistant to Powdery Mildew under greenhouse conditions.
8. Excellent postproduction longevity with plants maintaining good condition for about 6 weeks under interior conditions.

The following characteristics differentiate the new cultivar from the parent cultivar Lea and other Elatior Begonias commercially known and used in the floriculture industry, namely the cultivar Sanne (disclosed in U.S. Plant Pat. No. 9,430).

1. Plants of the new cultivar are more freely branching, more uniform and stronger than plants of the cultivar Sanne.
2. Plants of the new cultivar are more vigorous and taller than plants of the cultivar Lea.
3. Plants of the new cultivar have longer petioles than plants of the cultivars Lea and Sanne.
4. Flowers of plants of the new cultivar are more fully double than plants of the cultivar Sanne.
5. Although similar in flower color, plants of the new cultivar have a darker pink petal margin that is not observed on plants of the cultivars Lea and Sanne.

6. Flowers of plants of the new cultivar are more cupped than flowers of plants of the cultivars Lea and Sanne.

The accompanying colored photograph illustrates the overall appearance and flower color of the new cultivar, showing the colors as true as it is reasonably possible to obtain in colored reproductions of this type. The photograph comprises a side perspective view of a typical potted plant of Dina. Actual flower and foliage colors may differ from flower and foliage colors in the photograph due to light reflectance.

The following observations, measurements, values, and comparisons describe plants grown in Loudon, N.H., during the winter under commercial practice in a glass-covered greenhouse. In the following description, color references are made to The Royal Horticultural Society Colour Chart except where general terms of ordinary dictionary significance are used.

Botanical classification: *Begonia×hiemalis* cultivar Dina.

Commercial classification: Elatior begonia.

Parentage: Naturally-occurring mutation of *Begonia× hiemalis* cultivar Lea.

Propagation:

*Type.*—By terminal cuttings.

*Time to initiate roots.*—Terminal cuttings root in 17 to 21 days at temperatures of 21C.

*Rooting habit.*—Root system is very strong, vigorous and develops rapidly. Roots are prolific and dense. Root texture is fine and fibrous.

Plant description:

*Plant form.*—Upright and spreading potted plant, freely branching with usually 5 branches per plant. Good stem and stem base strength. Flowers are fully double and abundant. Plants flower continuously under warm night temperatures.

*Growth habit.*—Moderate vigor. Suitable for 10 to 15-cm containers. Under optimal environmental conditions, 13 to 14 weeks are required to produce proportional 12.5-cm potted plants from terminal cuttings that are directly-stuck in the container. Vegetative shoots are formed at basal nodes and flowering shoots are formed at upper nodes.

*Plant height.*—About 20 cm in a 12.5-cm pot.

*Plant width.*—About 20 cm in a 12.5-cm pot.

*Stem description.*—Lateral branch length: About 13 cm. Lateral branch diameter: 5 to 10 mm. Internode length: 2 to 3 cm. Stem color: 139C. Stem texture:

Sparsely pubescent. Stem strength: Very strong. Stem base strength: Very strong.

*Foliage description.*—Leaf arrangement: Simple, alternate. Leaf length: 7 to 8 cm. Leaf width: 9 to 10 cm. Leaf shape: Cordate. Leaf apex: Acute. Leaf base: Obtuse. Leaf margin: Serrate. Leaf texture: Upper surface: Smooth, leathery, glabrous. Lower surface: Leathery, sparsely pubescent. Leaf color: Young foliage, upper surface: 139A. Young foliage, lower surface: 139C. Mature foliage, upper surface: 139A. Mature foliage, lower surface: 138B. Petiole length: 1to 4 cm. Petiole diameter: 4 to 5 mm. Petiole color: 139D. Venation pattern: Palmate, smooth on abaxial surface, prominent on adaxial surface. Venation color: Upper surface: 141C. Lower surface: 139C.

Flower description:

*Flowering habit.*—Flowers arranged in racemes. Many racemes in flower simultaneously. Flowering continuous under warm(higher than 18° C.) night temperatures.

*Time to flower.*—Under optimal environmental conditions, usually 4 to 6 weeks are required.

*Natural flowering season.*—Plants will flower year around regardless of daylength, however plants will flower earlier and more abundantly if daylength is 12 hours or less.

*Quantity of flowers.*—Six to 8 flowers per raceme, up to 50 flowers at various stages of development may be present per 12.5-cm pot.

*Flowers.*—Shape: Circular, somewhat cupped. Diameter: 2.5 to 4 cm. Height: 1.5 to 1.7 cm. Aspect: Erect.

*Peduncle.*—Length: 5 to 12 mm. Strength: Good. Color: 147C. Angle: About 45° C.

*Flower bud.*—Shape: Ovoid. Diameter: 5 mm. Length: 5 mm. Rate of opening: 3 to 5 days. Color: 49B with 50C at margin.

*Petals.*—Arrangement: Rosette. Shape: Cupped to flat, rounded. Quantity per flower: 8 to 20. Length: 1.5 to 2 cm. Width: 1.5 to 2 cm. Apex: Rounded, obtuse. Color: When opening: Upper surface: 52C. Lower surface: 54B fading to 54D towards base. Fully open: Upper surface: 51C with darker pink, 51B, margin. Lower surface: 54B fading to 54D towards base. Margin: Entire. Texture: Smooth, velvety, glabrous.

*Sepals.*—Arrangement: Opposite. Shape: Oval, flat. Quantity per flower: 2. Color: Upper surface: 139C. Lower surface: 139C. Apex: Slightly pointed. Margin: Entire. Texture: Thin, transparent.

*Reproductive organs.*—Stamens: None. Pistils: None.

Postproduction longevity: Individual flowers generally maintain good condition for 2 to 3 weeks. Whole plants generally maintain good condition for about 6 weeks under interior conditions.

Disease resistance: Plants of the cultivar Dina are resistant to Powdery Mildew.

Seed production: Seed production has not been observed as reproductive organs are not formed.

I claim:

1. A new and distinct Elatior Begonia plant named Dina, as illustrated and described.

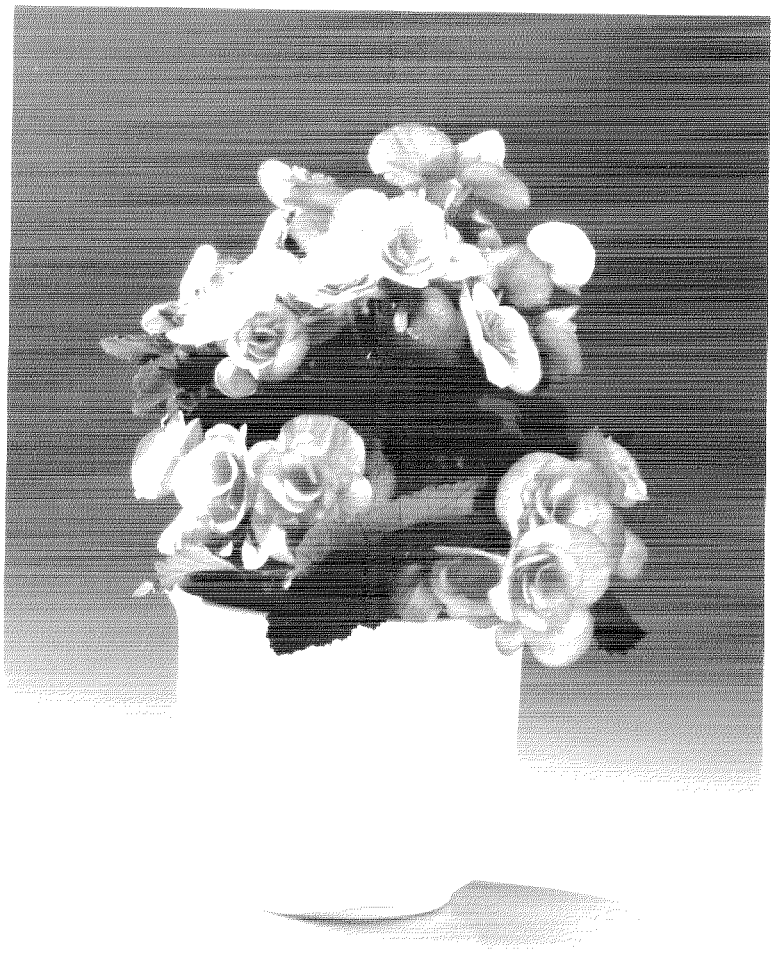

* * * * *